United States Patent [19]

Dorogi et al.

[11] Patent Number: 4,777,599

[45] Date of Patent: Oct. 11, 1988

[54] VISCOELASTOMETRY OF SKIN USING SHEAR WAVE PROPAGATION

[75] Inventors: Peter L. Dorogi, Washington, D.C.; Edmund M. Buras, Jr., Silver Spring, Md.

[73] Assignee: Gillette Company, Boston, Mass.

[21] Appl. No.: 705,655

[22] Filed: Feb. 26, 1985

[51] Int. Cl.$^4$ .............................................. A61B 10/00
[52] U.S. Cl. ................................ 364/413.02; 128/774
[58] Field of Search ................. 364/415; 128/774, 653

[56] References Cited

U.S. PATENT DOCUMENTS

| | | | |
|---|---|---|---|
| 4,177,798 | 12/1979 | Levegue et al. | 128/774 |
| 4,250,894 | 2/1981 | Frei et al. | 128/774 |
| 4,682,608 | 7/1987 | De Rigal et al. | 128/774 |

FOREIGN PATENT DOCUMENTS

| | | | |
|---|---|---|---|
| 0091768 | 10/1983 | European Pat. Off. | 128/774 |
| 0745503 | 7/1980 | U.S.S.R. | 128/774 |

OTHER PUBLICATIONS

D. Fitzgeorge, "An Instrument for Measuring Intracorneal Adhesion of the Stratum Corneum of Human Skin", Oct. 1976; p. 105–106.
The Journal of Investigative Dermatology, vol. 82, No. 1, 1984–"Changes with Age in the Moisture Content of Human Skin"—Russell O. Potts, Ph.D., Edmund M. Buras, Jr., M. S. and Dan A. Chrisman, Jr., B. S.
J. Biomechanics, vol. 16, No. 6, pp. 365–372; "The Dynamic Mechanical Properties of Human Skin in Vivo'"—Russell O. Potts, Dan A. Chrisman, Jr., and Edmund M. Buras, Jr.
Fourth International Symposium on Bioengineering and the Skin, Besancon, France, Sep. 7–9, 1983; "Shear Wave Propagation: Non-Invasive Measurement of the Effects of Moisture Content of Human skin"-Edmund M. Buras, Jr.
Journal of Colloid Science, 18, 1963, pp. 757–771; "Propagation Characteristics of Capillary Ripples, II. Instrumentation for Measurement of Ripple Velocity and Amplitude"; J. Adin Mann, Jr. and R. S. Hansen.
Journal of Colloid Science, 18, 1963, pp. 805–819; "Propagation Characteristics of Capillary Ripples, III. Capillary Ripple Velocity and Attenuation Dispersion of Clean Water Surfaces and on Various Monolayers"; J. Adin Mann, Jr. and R. S. Hansen.
J. Soc. Cosmet. Chem, 1–19 (Jan./Feb. 1984), pp. 1–19; "Measurement of Skin Condition by Sonic Velocity"; R. Marc Dahlgren and W. H. Elsnau.
The Journal of Investigative Dermatology, vol. 69, No. 3, 1977; pp. 282–286; "Viscoelastic Properties of Intact Human Skin: Instrumentation, Hydration Effects, and the Contribution of the Stratum Corneum", M. S. Christensen, Ph.D., C. W, Hargens, III, S. B., S. Nacht, Ph.D. and E. H. Gans, Ph.D.

Primary Examiner—Jerry Smith
Assistant Examiner—Kim T. Tbui
Attorney, Agent, or Firm—Burns, Doane, Swecker & Mathis

[57] ABSTRACT

The properties of the skin are quantitatively defined by inducing shear waves in the outermost layers of the skin. The response of the skin to these waves is measured in terms of changes in the phase and amplitude of the waves as they propagate through the skin. From such measurements, various relationships of the viscoelastic properties of the skin are determined. These viscoelastic properties are expressed in terms of the viscosity of each of the stratum corneum and epidermal layers as well as the elasticity of the stratum corneum. These quantitative parameters can then be used to generate various moduli which can be displayed in a manner that enables changes in such properties to be readily perceived.

28 Claims, 6 Drawing Sheets

LOG G2 vs LOG G1

LOG G2 vs LOG G1

LOG G2 vs LOG G1

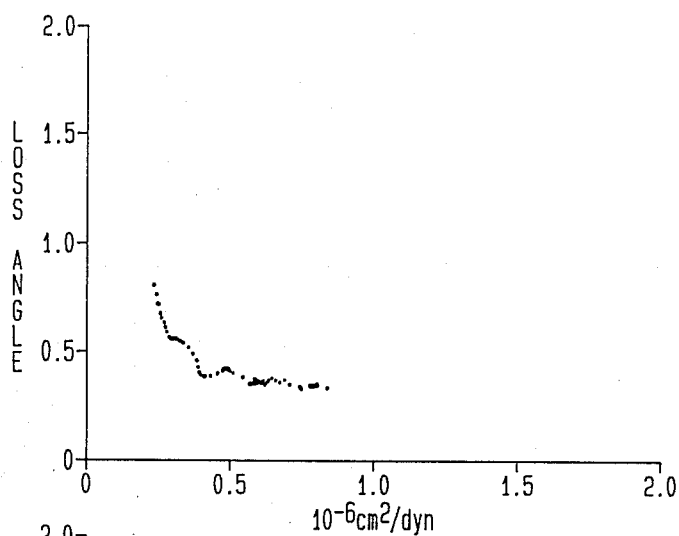
FIG. 6A COMPLIANCE
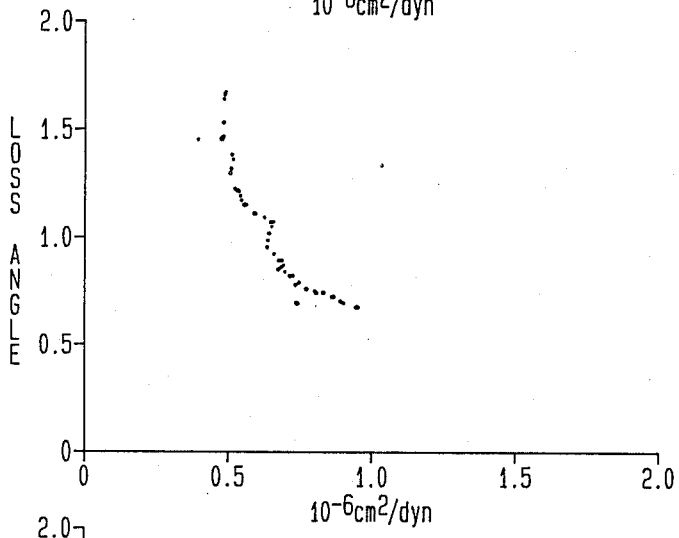
FIG. 6B COMPLIANCE
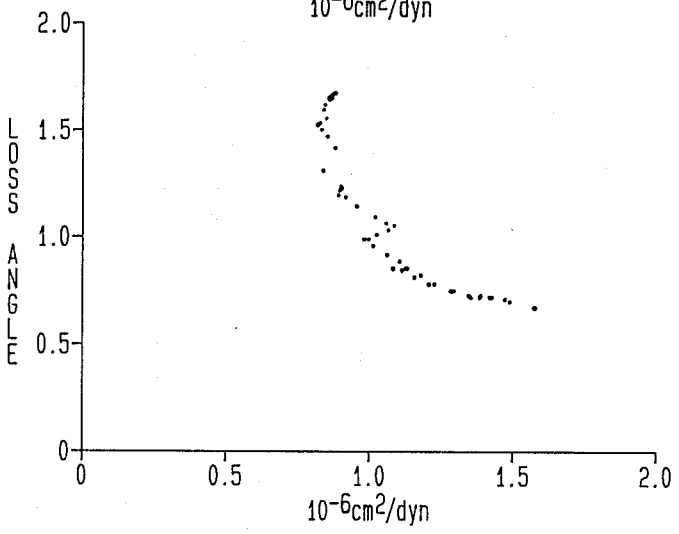
FIG. 6C COMPLIANCE

VISCOELASTOMETRY OF SKIN USING SHEAR WAVE PROPAGATION

BACKGROUND AND OBJECTS OF THE INVENTION

The present invention is directed to a non-invasive technique for measuring the properties of skin, and more particularly is concerned with the measurement of the viscoelastic properties of the stratum corneum and subjacent viable epidermis layers of the skin as a means for evaluating the effects which aging, disease, various products and climates have upon the skin.

It is desirable to be able to measure various properties of the skin for the purpose of evaluating the efficacy of skin care products. For example, it is useful to know how a cosmetic or moisturizing lotion affects the youthfulness, smoothness or moistness of the skin, or how effective a specific shaving instrument, pre-shave lotion or after-shave lotion is at reducing irritation. However, due to the lack of valid physical measures in the past, clinical studies of product efficacy often depended on visual and tactile grading, for example by moving the fingertips across the skin surface. These measures are necessarily qualitative and the least significant difference that can be detected depends on the evaluator's experience and on the reproducibility of his judgments. An even greater problem arises from intercomparisons and pooled data from tests graded by different individuals; the built-in variability which exists in such product tests requires large, costly studies before high confidence levels about test results can be reached.

Accordingly, it is a general object of the present invention to provide a novel method for providing a quantitative definition of mechanical properties of the skin using a noninvasive, in vivo measurement technique.

Toward this end, research has been conducted to determine mechanical properties of the skin by evaluating its effect upon shear waves. See Potts et al, "The Dynamic Mechanical Properties of Skin In Vivo", *J. Biomechanics*, Vol. 16, No. 6, pp. 365–372, 1983. By investigating the propagation and attenuation of shear waves at a number of different frequencies, the propagation velocity and damping length for the skin can be determined at each frequency. It has been found that these two properties are sensitive to the degree of moisturization of the skin. Results of tests utilizing the shear wave measurement technique suggest that aged skin has a lower water content than the skin of younger people. See Potts et al, "Changes With Age in the Moisture Content of Human Skin", *J. Investigative Dermatology*, Vol. 82, No. 1, pp. 97–100, 1984.

While the basic research conducted by Potts et al indicates that it is possible to determine mechanical properties of skin, it is desirable to further improve upon such research. More specifically, propagation velocity and damping length are frequency dependent parameters that do not readily lend themselves to anatomical interpretation for the purpose of evaluating the efficacy of various products. In particular, it is desirable to quantitatively define properties of the skin in terms which can be more clearly associated with elements of human perception.

Therefore, it is a more specific object of the invention to provide such a method which is capable of measuring the properties of the stratum corneum and epidermal layers of the skin in a manner which enables the effects of a skin care instrument or product to be evaluated.

It is a further object of the invention to provide such a method which is capable of measuring the viscoelastic properties of each of the stratum corneum and subjacent viable epidermis individually with the use of shear waves to facilitate the development and evaluation of conditioners that are directed to specific skin problems.

Toward this end, it is a particular object of the present invention to provide a discrete-element mechanical model which describes the skin, and to define the physical properties of the skin in terms of frequency-independent constants related to such model.

It is another object of the present invention to provide quantitative data which can be correlated with human-perceptible qualities such as smoothness and moistness.

It is yet a further object of the invention to provide a novel method of displaying the results of the quantitative analysis of skin properties in such a manner as to be easily understood by the average consumer of skin care products.

BRIEF STATEMENT OF THE INVENTION

Briefly stated, these objects and their attendant advantages are achieved in accordance with the present invention by inducing shear waves in the outermost layers of the skin. At low amplitudes and relatively low frequencies the outermost layers of the skin behave in a manner similar to a simple mechanical model composed of discrete elements. The response of the skin to these waves is measured in terms of changes in the phase and amplitude of the waves as they propagate through the skin. From such measurements the parameters of the mechanical model, and hence the viscoelastic properties of the skin, are determined. Preferably, these viscoelastic properties are expressed in terms of the viscosity of each of the stratum corneum and epidermal layers as well as the elasticity of the stratum corneum. These quantitative parameters can then be used to estimate various dynamic moduli which can be displayed in a manner that enables changes in such properties to be readily evaluated.

Further features of the invention are described hereinafter with reference to the accompanying drawings.

BRIEF DESCRIPTION OF THE DRAWINGS

FIGS. 6A, B and C are graphs illustrating another form for the display of the information;

DETAILED DESCRIPTION

In the following description, particular reference is made to the invention in the context of evaluating the efficacy of skin care products, in order to facilitate an understanding of the invention. However, it will be appreciated that the invention has other useful applications, such as diagnosing skin diseases and determining skin properties for duplication in the development of prosthetic devices, for example.

Figure 1:
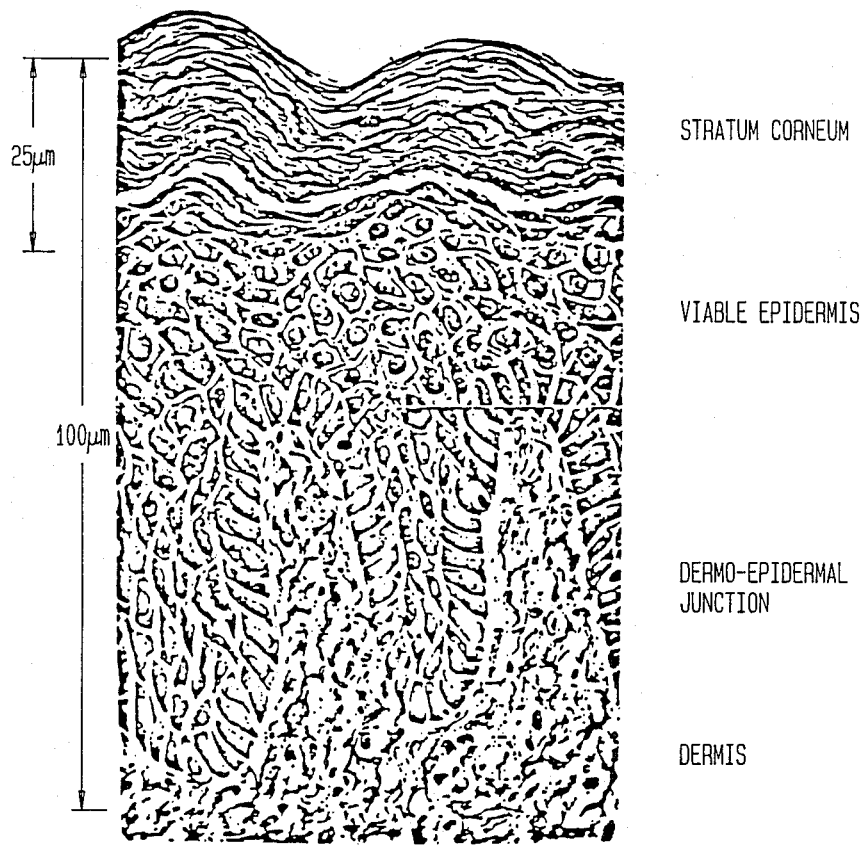
FIG. 1 is a cross-sectional schematic representation of the uppermost layers of the skin.

A cross sectional schematic represenation of the outermost layers of the skin, down to a depth of about 100 micrometers, is shown in FIG. 1. The exterior surface of the skin comprises the stratum corneum, which can have a thickness of about 10-15 micrometers. Below this layer lies the viable epidermis, which might extend to 40-75 micrometers below the surface. The innermost dermis layer is conjugated with the epidermis at the dermal-epidermal juction.

It is reasonable to assume that human perception of the feel and appearance of skin is a judgement mainly of the skin's outermost layer, the epidermis, including the harder, drier stratum corneum seen from the outside. The moister, living tissue in the underlying epidermis consists of cells which are gradually pushed outwards, become keratinized and die, replenishing the stratum corneum. In most cases of practical interest, cosmetic qualities pertain primarily to the stratum corneum and probably reflect the chemical composition of this layer. The latter is in turn determined by the biochemical history of the epidermis, and by external influences on the skin, such as the environment and cosmetic treatment.

The perceptible attributes of skin are related to the thickness and moisture content of the stratum corneum. However, changes in skin chemistry are also mirrored in the mechanical properties of the epidermis, as evidenced by increased stiffness and viscosity in aged skin. It therefore follows that negative changes in skin tone, and resultantly in skin appearance, caused by exposure to cold weather, sunlight, and natural aging process and shaving irritation, as well as their reversal, can be monitored by measuring stiffness and viscosity.

Figure 2:
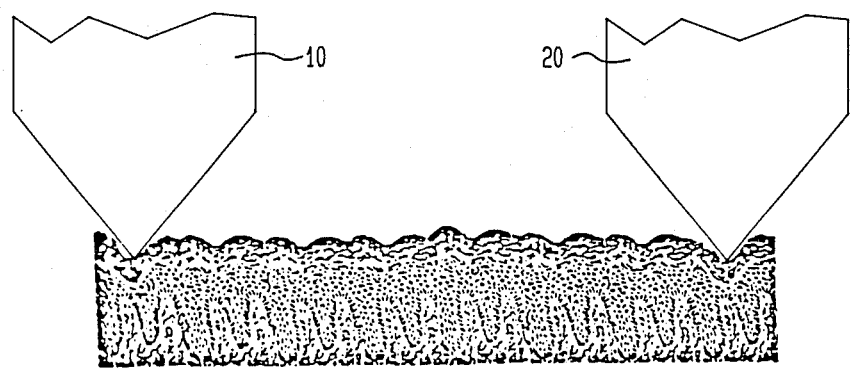
FIG. 2 is a view similar to FIG. 1 illustrating the probes that are used to induce and detect shear waves in the skin.

In accordance with the invention, these measurements are carried out by inducing shear waves in the skin and detecting the skin's effect on the propagation of waves. Referring to FIG. 2, the shear waves are induced by means of a vibrating probe 10 which oscillates in a direction perpendicular to the plane of the figure. This movement results in shear waves that travel in lateral directions and are detected on the skin surface by sensing probes 20 located at known distances from the vibrating probe 10.

Preferably, the amplitude of the vibrations of the probe 10 are relatively small, in the range of 20-30 micrometers, most preferably 25 micrometers, peak to peak, which is about the thickness of one skin cell. By keeping the amplitude of these vibrations small, the depth of the mechanical disturbance into the skin is also kept small, i.e. it is approximately the same magnitude. Accordingly, waves which are detected at the sensor 20 will have traversed only the stratum corneum and the upper viable epidermal tissue.

By limiting the depth of the waves in this manner, interpretation of the data that is obtained is greatly simplified. The detected "stiffness" is localized principally in the stratum corneum. The less keratinized, softer tissue below the stratum corneum contributes principally as a "damping" medium wherein little mechanical energy can be stored. For example, shear waves of high frequency are damped out in the viable epidermis due to frictional effects. On the other hand, the keratinized tissue of the stratum corneum imparts a high degree of elasticity to this tissue, which allows transmission of the rapid motion of high-frequency waves.

Figure 3:
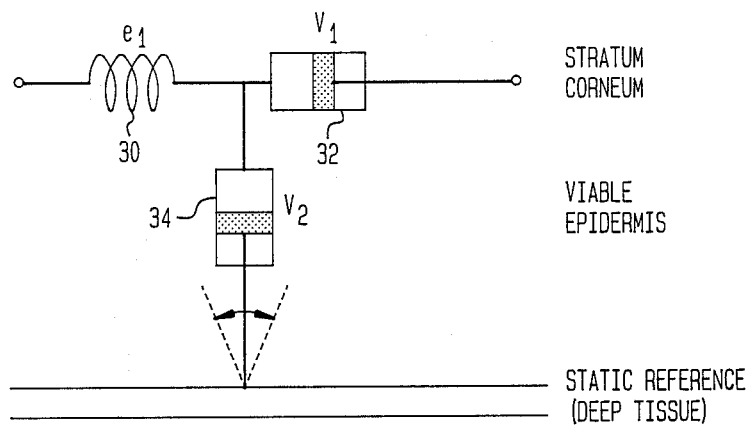
FIG. 3 is a schematic illustration of a mechanical model which describes the elasticity and viscosity of the outer layers of the skin.
Figure 4:
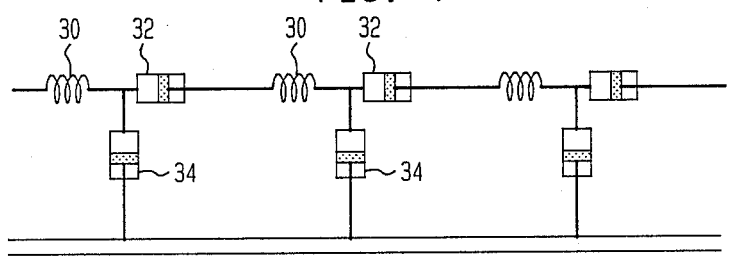
FIG. 4 is a schematic illustration of a wave conduction model for the skin.

These characteristics of the outermost layers of the skin under such conditions allow them to be analogized to the simple schematic model shown in FIGS. 3 and 4. FIG. 3 shows the mechanical model which describes stress-strain relations over dimensions on the order of 20-30 micrometers. This model comprises a spring 30 having a modulus of elasticity $e_1$, and connected in series with a dashpot 32 having a viscosity $V_1$. The junction of these two elements is tied to a static reference (representing deep skin tissue) by a second dashpot 34 having a viscosity $V_2$. FIG. 4 shows the mechanical model for simulating wave conduction through the epidermis. Basically, this model comprises a number of the unit models of FIG. 3 chained in an end-to-end relationship.

At low frequencies, e.g., less than 500 Hz, the inelastic, viscous element 34 stretches and compresses as the top segment, which has elastic as well as viscous properties, stretches and shrinks. Therefore, at low frequencies the lower segment reduces some of the motion of the upper segment, but the lower segment also moves. As the speed of motion induced in the model, i.e. at the ends of the top segment, increases the frictional elements 32 and 34 are less able to move, the dissipate the kinetic energy as heat. At very high frequencies, the lower segment dissipates all energy imparted to it, but the elastic element 30 in the top segment is still able to store some of the energy, which helps to recover the original length during the "release" part of the cycle. Therefore, even though the stratum corneum is less fluid (more viscous) than the tissue underneath, its elastic quality allows conduction of wave motion at frequencies so high that movement in the viable tissue is totally damped out.

Accordingly, this model, and the analogous layers of the skin, can be quantitatively described in terms of three constants: the modulus of elasticity $e_1$ of the stratum corneum and the viscosities $V_1$ and $V_2$ of each of the corneum and the subjacent viable epidermis. In practice, these three properties are determined by measuring the effect which the skin has on the propagation of the shear waves. Specifically, the effect of the skin is to change the phase of the wave by an angle $\Phi_d$ (where d is the distance between the two probes 10 and 20) and to reduce the amplitude of the wave by an amount $e^{-\lambda d}$, which becomes smaller as d increases. In practice, the detector signal may be altered by mechanical coupling between either or both of the probes 10 and 20 and the skin. To eliminate any common-mode apparatus and coupling contributions, it is preferable to utilize two detector probes spaced at two different distances $d_1$ and $d_2$ from the vibrating probe 10. When the signals from each of the detectors is subtracted, only properties corresponding to a length $d_2-d_1$ is the skin will be reflected in the data which is obtained. Thus, the phase difference will be $\Phi_{(d_2-d_1)}$ and the damping of the waves will be defined by $e^{-\lambda(d_2-d_1)}$.

In practice the phase delay and amplitude decay measurements are carried out at a number of different oscillating frequencies. For example, 128 discrete frequencies in the range of 8-1024 Hz can be used to provide 128 phase delay and amplitude decay measurements. The measurements taken at lower frequences, e.g. below about 500 Hz, provide information about the viable epidermis while those above about 500 Hz relate primarily to the stratum corneum.

With this information it is possible to determine the dynamic compliance G of the material, which is a measure of the amount of "give" of the material under an applied stress or strain. The dynamic compliance is comprised of two components, an in-phase factor $G_1(\omega)$ representative of an elastic medium and an out-of-phase factor $G_2(\omega)$ representative of the viscous medium. These two components are defined as follows:

$$G_1(\omega) = \frac{[\phi'(\omega)]^2 - [\lambda(\omega)]^2}{\rho\omega^2} \quad (1)$$

$$G_2(\omega) = \frac{-2\phi'(\omega)\lambda(\omega)}{\rho\omega^2} \quad (2)$$

where $w=2\pi f$ (f being the frequency of the oscillations of the probe 10) $\phi'(\omega)=\omega\phi_{d2-d1}(\omega)/[2\pi(d_2-d_1)]$, and $\rho$ is the density of the material in g/cm$^3$.

These two compliance components are related to the three characteristic constants of the mechanical model as follows:

$$G_1(\omega) = \frac{e_1}{e_1^2 + V_1^2\omega^2} \quad (3)$$

$$G_2(\omega) = \frac{\left(\frac{V_1}{V_2}\right)(V_1 + V_2)\omega + \frac{e_1^2}{V_2\omega}}{e_1^2 + V_1^2\omega^2} \quad (4)$$

Rearranging Equation 3 as $$\omega^2 G_1(\omega) = \left(\frac{e_1}{V_1}\right)^2 G_1(\omega) - \frac{e_1}{V_1^2} \quad (5)$$

reveals that a plot of $\omega^2 G_1(\omega)$ against $G_1(\omega)$ should be linear. Thus, $e_1$ and $V_1$ can be calculated as linear regression statistical parameters. Furthermore, $V_2$ is calculable from Equation 4:

$$\frac{1}{V_2} = \omega G_2(\omega) - \frac{V_1}{e_1}\omega^2 G_1(\omega). \quad (6)$$

Accordingly, all three of the frequency-independent constants $e_1$, $V_1$ and $V_2$ can be calculated from the phase and amplitude information obtained by the detector probes.

These constants can be used to evaluate the effects which various conditioners have upon the skin. In particular, $e_1$ can be labeled the stratum corneum rigidity modulus and measures the resistance to bending of the keratinized part of the epidermis. The stratum corneum viscosity, $V_1$, measures resistance to plastic flow in the keratinized part of the epidermis, and the viable epidermis viscosity, $V_2$, measures the corresponding property of the living, non-keratinized epidermal tissue. Table I below lists an example of data which was obtained from the forearm skin of a 38-year old woman on untreated and various chemically treated sites.

TABLE I

EPIDERMAL MECHANICAL PARAMETERS; QUANTITATIVE MEASURES OF CONDITION EFFECTS ON THE EPIDERMIS

| | PARAMETERS | | |
|---|---|---|---|
| | Stratum corneum | | Viable epidermis |
| TREATMENT | $e_1$ (10$^5$ dyn/cm$^2$) | $v_1$ (poise) | $v_2$ (poise) |
| Untreated | 5.6 | 280 | 145 |
| Petrolatum | 4.7 | 259 | 118 |
| Mineral Oil | 5.2 | 200 | 122 |
| Glycerin | 14.0 | 893 | 269 |
| Water | 3.3 | 204 | 159 |
| Urea | 66.0 | 1509 | 224 |
| Lactic Acid | 8.7 | 328 | 146 |

As can be seen from the table, the values of the mechanical parameters differ with the nature of the treatment, showing different types of interactions with the epidermis.

The significance of these parameters in product evaluation are better understood once their roles in sensory evaluation of skin are known. It is therefore desirable to transpose mechanical evaluation of the epidermis from the realm of wave propagation to the realm of human experience, such as the dynamic forces encountered in shaving and in feeling skin with one's fingers.

In a purely elastic material, the ratio of stress to strain is independent of time. However, viscoelastic materials, such as skin, will continue to stretch as long as a force is present. Any deformation other than that which is compensated for by elastic bonds, for example, elastic intercellular bonds and elastic deformability of the cells themselves, is due to the fluid components of the epidermis. Excessive stress on the epidermis under an applied force is normally prevented by the fluid response of the tissue. Hence, healthy epidermis appears to respond less stiffly (lower $e_1$) and with more plastic flow (lower $V_1$ and $V_2$) than aged epidermis. Usually, a higher creep indicates better perceived skin quality.

For example, when a blade is dragged along the skin surface during shaving, the frictional force at the blade-skin contact site produces a pulling force on the epidermis, in addition to which some of the less moist (dead) stratum corneum cells are removed. It can be presumed that the shave will be less damaging to skin when the epidermis is more able to comply with the blade. In other words, the epidermis should provide a compliant surface for the blade. Deformations at the blade-skin contact site should be mainly fluid, with a large degree of creep.

Similar arguments apply to the feel of the skin when it is manipulated by rubbing a finger gently on its surface. A pliant epidermis will feel smooth because it drags along with the finger. Dragging of the epidermis results in lowering of the frictional forces, which is interpreted as "smoothness".

Accordingly, it is possible to correlate the measured viscoelastic parameters with those properties of skin that are perceived by individuals. More particularly, "smoothness" and "moistness" are mainly related to the mechanical properties of the outermost skin layer, the stratum corneum. On the other hand, the attribute "youthfulness" is closely related to skin fluid components, which lie below the stratum corneum. Table II below provides a quantitative correlation between these properties, based on the results of a panel study.

TABLE II

CORRELATIONS BETWEEN HUMAN PERCEPTION AND THE
INSTRUMENTAL MEASUREMENTS
(SQUARE OF REGRESSION COEFFICIENTS)

| HUMAN PERCEPTION ANALYSIS | *STRATUM CORNEUM* STIFFNESS | *STRATUM CORNEUM* VISCOSITY | DEEP EPIDERMAL VISCOSITY | TOTAL EPIDERMAL CREEP |
|---|---|---|---|---|
| Youthfulness | — | — | 0.77 | 0.74 |
| Smoothness | 0.76 | 0.62 | 0.59 | — |
| Moistness | 0.83 | 0.74 | 0.67 | 0.59 |

These numbers are interpreted as, for example, 77% of the perceived differences in "youthfulness" of skin can be accounted for by the variation in deep epidermal viscosity among the sites tested. (Only coefficients greater than 0.50 are shown in the above table.)

Thus it will be appreciated that the viscoelastic data obtained from the shear wave measurements can be utilized to gain insight into the influence of conditioners on the skin. In a first embodiment of the invention, the viscoelastic parameters can be determined for untreated skin and displayed. The skin can then be treated with a selected agent or conditioner, the efficacy of which is to be analyzed, and the viscoelastic parameters for the treated skin displayed alongside those of the untreated skin for comparison, for example in the manner shown in Table 1. Changes in the measured properties provide an indication of the specific effects of the conditioner on the skin.

While a trained evaluator may be able to readily correlate changes in the measured parameters with specific properties of the skin, it will be appreciated that an average lay consumer who wishes to determine the efficacy of a product on his or her skin at a point of sale may not comprehend the meaning of such absolute numbers. Accordingly, in further embodiments of the invention the viscoelastic data that is obtained from the shear wave measurements is displayed in a fashion that is more readily understandable to a person with limited technical understanding.

Figure 5A:
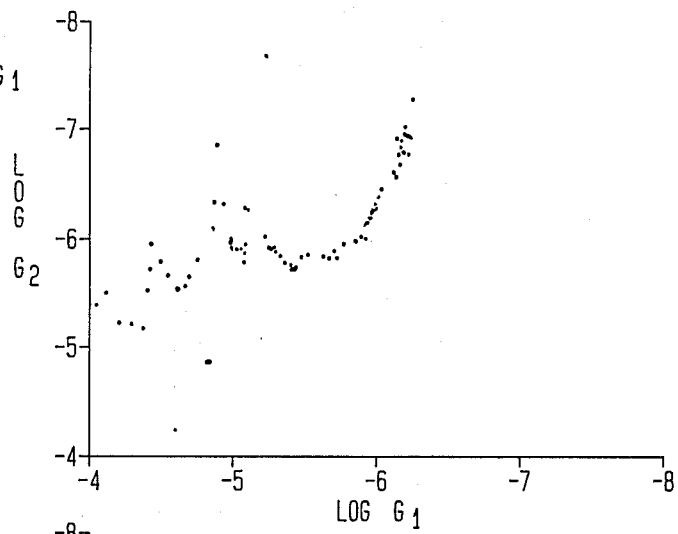
FIGS. 5A, B and C are graphs illustrating one manner for displaying the information obtained about the skin.
Figure 5B:
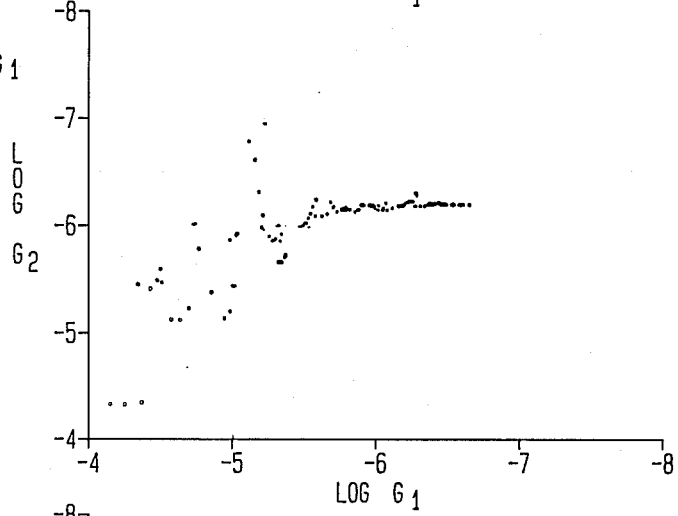
Figure 5C:
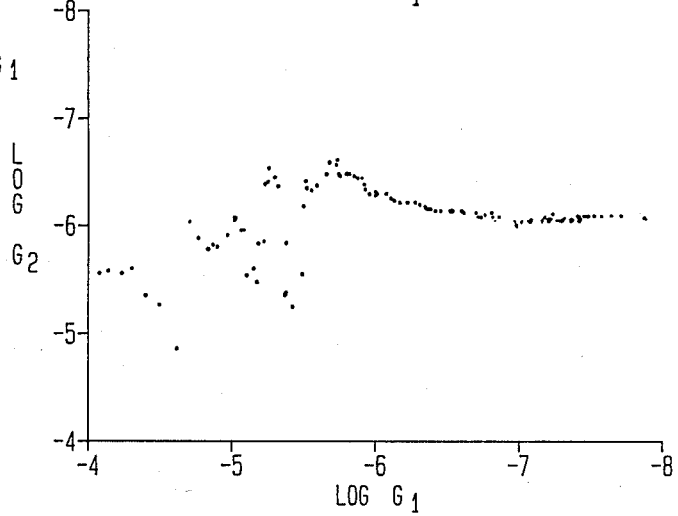

In one such embodiment the in-phase and out-of-phase dynamic compliance components $G_1$ and $G_2$ are plotted against one another on a log-log scale as shown in FIGS. 5A, 5B and 5C. The $G_2$ scale on the vertical axis decreases in the upward direction and the $G_1$ scale on the horizontal axis decreases in the rightward direction. Each dot on the graph represents the data obtained at one of the multiple measurement frequencies. The information provided by such a display is useful in diagnosing the condition of the epidermis. Basically, resistance to flow (viscosity) is depicted on the vertical scale and resistance to stretching (stiffness) is represented on the horizontal scale.

At low frequencies, the numerator in Equation 3 is roughly constant with frequency, and $G_1(\omega)$ and $G_2(\omega)$ decrease in proportion with increasing frequency. As a result that display tends to be a 45-degree line at low frequencies. Above a certain frequency range $V_1^2\omega^2 >> e_1^2$, and the change in $G_1(\omega)$ will be greater than the change in frequencies, thus giving a characteristic "two-phase" curve as shown in FIGS. 5A, 5B and 5C.

Whether the curve becomes horizontal, or "flat", depends on the viscoelastic properties of the epidermis. A relatively high $e_1$ gives a 45° response throughout; a low $V_1$ also results in a 45° slope. Skin conditioners tend to lower $e_1$, giving a larger flat portion in the display. Thus, changes in the mechanical properties of the skin are displayed as slope changes. A "lowering" of the flat portion on the vertical scale means decreased viscosity (increased fluidity). The ideal response to a skin conditioner is some flattening and a slight lowering of the dot pattern in the high resistance region. Too much of a rightward and/or downward shift indicates that the epidermis is losing too much of its elasticity. For example, no change on the vertical scale, but a large shift to the right from one measurement to the next indicates no change in $G_2(\omega)$. This means no change in viscosity but a large decrease in $e_1$ (i.e., a large decrease in stiffness).

Furthermore, the arrangement of the dots in the graph indicates the degree of tissue homogeneity or organization. Sharply defined lines reflect a healthy epidermis, whereas more scattered dots indicate a less regular structure prevalent in dry or chapped skin.

The particular displays illustrated in FIGS. 5A, 5B and 5C represent measurements taken from the forearm skin of a 23 year old female in an untreated state and five minutes after the application of two different skin conditioners, respectively. FIGS. 5B and 5C reveal that both conditioners have changed the high-frequency response from "sloped" to "flat", indicating that the viscous plateau has been reached. In FIG. 5B the total resistance has been essentially unchanged, but most of the force is accommodated by flow, i.e. the epidermis stretches more easily. For the conditioner shown in FIG. 5C the total resistance has greatly decreased, with a very large drop in the resistance to stretching. This skin will feel too lifeless, or "mushy".

A different type of display, referred to as a "Viscogram", is illustrated in FIGS. 6A, 6B and 6C. In this display, the vertical scale represents relative fluidity, or loss angle, which is defined as $G_2/G_1$. The horizontal scale reflects the total compliance of the material at a frequency, and is defined as:

$$G^* = \sqrt{[G_1(\omega)]^2 + [G_2(\omega)]^2}$$

This type of display shows primarily stratum corneum characteristics and is useful in defining viscosity and elasticity changes. More specifically, if the pattern on the display shifts to the right the material has become more pliant. Conversely, a shift to the left means the material has become harder or stiffer. The vertical scale is a measure of $(V_1)^2/e_1$ and when used in conjunction with a display of the type shown in FIGS. 5A, 5B and 5C can be used to evaluate the relative contributions of $V_1$ and $e_1$.

The particular examples illustrated in FIGS. 6A, 6B and 6C correspond to the same test subject represented in FIGS. 5A, 5B and 5C, i.e., skin which is untreated and then treated with two different conditioners. The conditioner effect shown in FIG. 6B has not changed the total resistance of the epidermis, but has raised the $(V_1)^2/e_1$ value. From FIG. 5B it is known that the fluidity of the tissue has increased ($V_1$ down), and that the epidermis stretches more easily ($e_1$ down). The Viscogram of FIG. 6B indicates that the reduction in stiffness is much greater than the reduction in viscosity. For the conditioner shown in FIG. 6C the total compliance is increased and the $(V_1)^2/e_1$ values have also increased. This indicates that the major change is a drop in $e_1$. The shift to the right is large, and the conditioner has actually made the skin feel too pliant. The conditioner effect shown in FIG. 6B is the more favorable.

Figure 7:
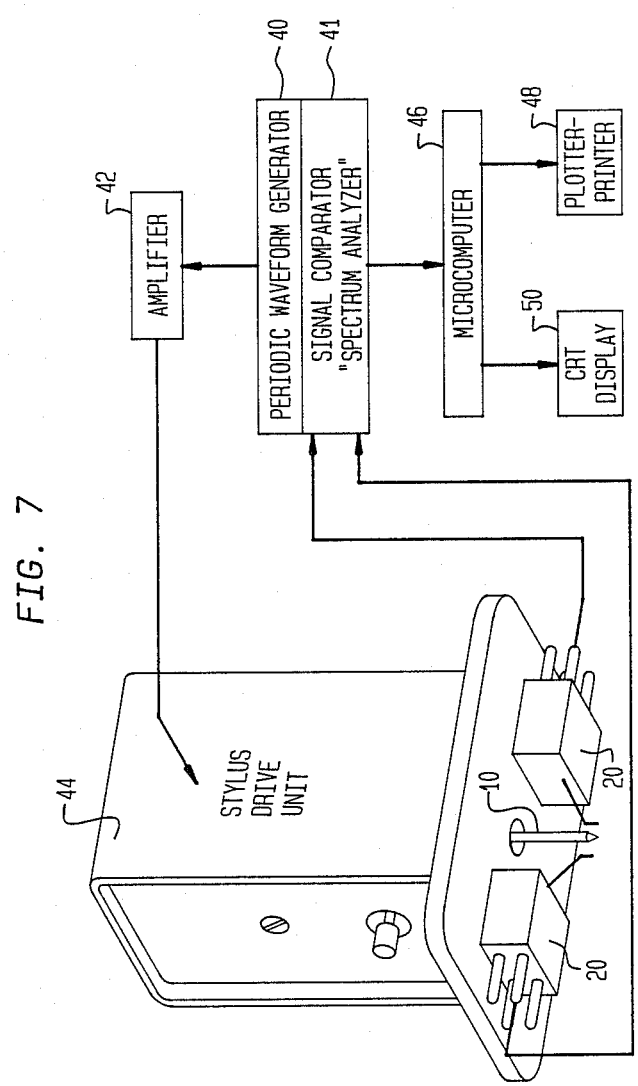
FIG. 7 is a block diagram of a system for carrying out the invention.

One example of a system for carrying out the foregoing technique is illustrated in FIG. 7. A waveform generator 40 includes a Fast Fourier Transform spectrum analyzer 41 and generates a periodic signal that is derived by summing the amplitudes of waves at a number of different frequencies, e.g. at every 8 Hz from 8 to 1024 Hz. This composite signal is amplified in an amplifier 42 and applied to drive the probe 10 through a transducer located in a stylus drive unit 44. For example, the drive unit can be of the type used to inscribe laterally variable grooves on monophonic phonograph records.

The shear waves induced in the skin by the oscillation of vibrating probe 10 are detected by sensing probes 20 located longitudinally at different distances from the vibrating probe. One sensing probe can be located 0.7 mm from the vibrating probe and the other one can be 2.0 mm from the vibrating probe, for example. These sensing probes actuate transducers, similar to the operation of a laterally responding monophonic phonograph cartridge, to generate electrical signals that are amplified and presented to the spectrum analyzer 41. The spectrum analyzer determines the ratio of the amplitudes of the two signals and their phase difference for each of the 128 different frequencies. This data is then presented to a microcomputer 46 which operates in accordance with the previously described principles to determine the viscoelastic constants of the skin and provide displays of the calculated properties.

Figure 8:
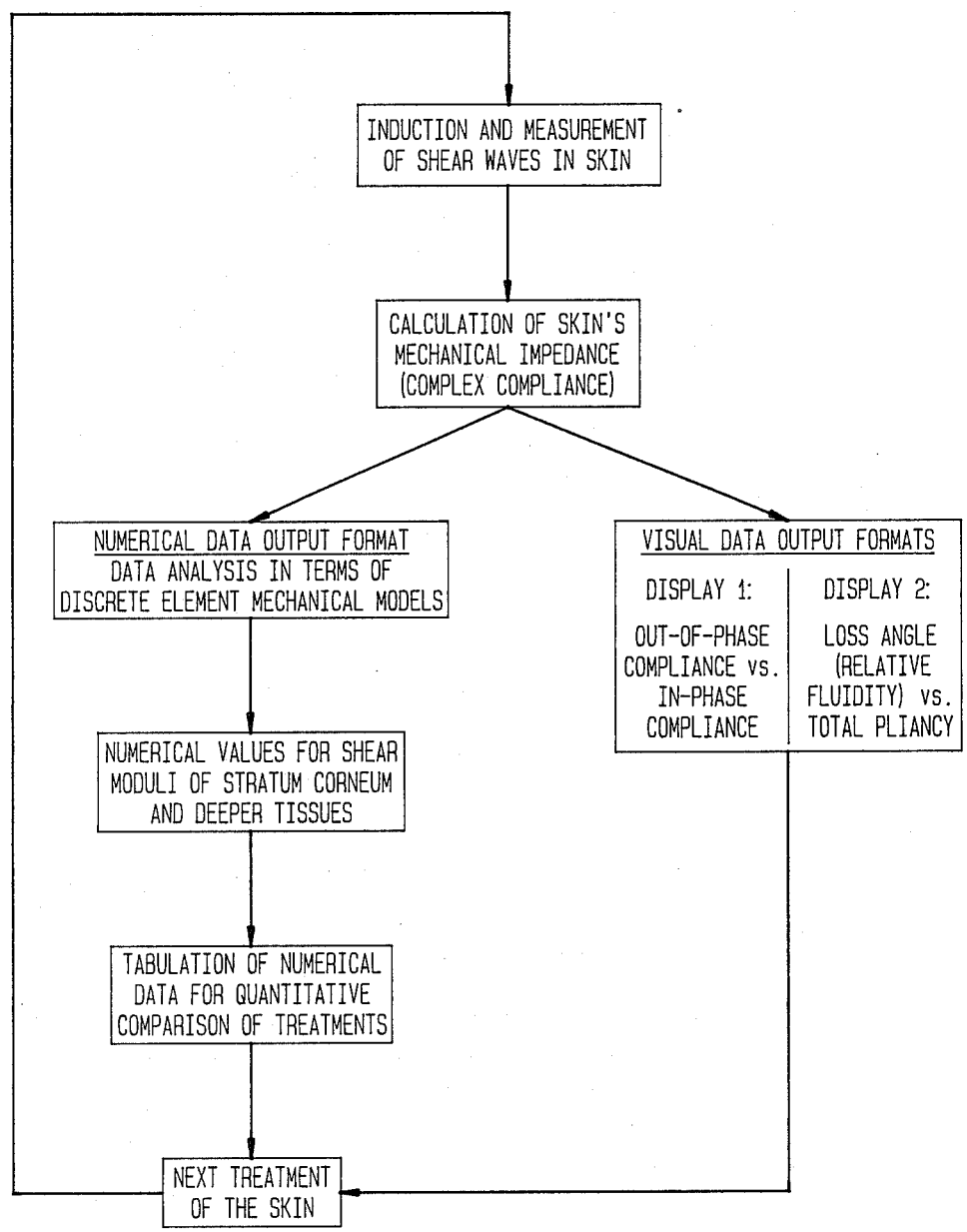
FIG. 8 is a flow chart depicting the operation of the system of FIG. 7.

A flow chart illustrating the general operation of the microcomputer is illustrated in FIG. 8. The microcomputer first instructs the waveform generator (which can be incorporated within the structure of the spectrum analyzer) to induce the shear waves in the skin and to measure the received data. From this information, the complex compliance of the skin is calculated in accordance with Equations 1 and 2. Then, in accordance with the type of information display that is required, the viscoelastic constants $e_1$, $V_1$ and $V_2$ can be determined (from Equations 5 and 6) and displayed on a printer/plotter 48 and on a CRT screen 50. Alternatively, or in addition, plots of the types shown in FIGS. 5 and 6 can be displayed. Subsequently, the skin can be treated with the product whose efficacy is to be measured, and the process repeated.

From the foregoing it will be appreciated that the present invention provides a useful approach to the quantification of the properties of the outermost layers of the skin in a manner which enables changes in the condition of the skin to be readily ascertained. Variations of the invention can be used to provide other types of information. For example, while the preferred amplitude of the induced oscillations of the skin is in the range of 20–30 micrometers to limit the measured response to the uppermost layers of the skin, a greater amplitude can be used to obtain additional information about deeper layers of the skin. However, in such a case the mechanical model which simulates the response of the skin might be different.

It will be appreciated by those of ordinary skill in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. A method for measuring and quantitatively indicating viscoelastic properties of the uppermost layers of the skin, comprising the steps of:
   including oscillations having an amplitude no greater than about 30 micrometers in the skin to generate shear waves that propagate through the skin;
   measuring changes in the phase and amplitude of the shear waves as they propagate through the skin;
   determining modulus of elasticity and viscosity constants descriptive of a discrete-element mechanical skin model on the basis of the measured changes in phase and amplitude; and
   displaying various complex moduli of elasticity and viscosity relationships.

2. The method of claim 1 wherein said oscillations have an amplitude in the range of 20–30 micrometers.

3. The method of claim 1 wherein said skin model comprises three discrete elements respectively defined by said constants, and wherein one of said constants is related to the rigidity of the stratum corneum layer of the skin, another of said constants is indicative of the viscosity of the stratum corneum, and a third constant is indicative of the viscosity of the viable epidermis layer which underlies the stratum corneum.

4. The method of claim 1 wherein said oscillations are induced at a plurality of frequencies.

5. The method of claim 4 wherein said plurality of frequencies are within the range of about 8 Hz to about 1024 Hz.

6. The method of claim 1 wherein said oscillations occur in a direction parallel to the surface of the skin and perpendicular to the direction of travel of said shear waves.

7. The method of claim 6 wherein said changes are measured at a location that is remote from the location at which the oscillations are induced in the skin, in the direction that is parallel to the surface of the skin.

8. A method for determining and indicating the effects of a product on the properties of the two outermost layers of the skin, comprising the steps of:
   (i) inducing strains in the skin to generate shear waves that propagate through the skin;
   (ii) measuring changes in the phase and amplitude of the shear waves as they propagate through the skin;
   (iii) determining quantities based on the modulus of elasticity for at least one of said layers and the viscosity of each of said two layers on the basis of the measured changes in phase and amplitude;
   (iv) displaying said quantities;
   (v) applying the product to the skin; and
   (vi) repeating steps (i) through (iv) after the product has been applied.

9. The method of claim 8 wherein said strains have an amplitude no greater than about 30 micrometers.

10. The method of claim 8 wherein said strains are induced at a plurality of frequencies.

11. The method of claim 10 wherein said plurality of frequencies are within the range of about 8 Hz to about 1024 Hz.

12. The method of claim 8 wherein said strains are induced in a direction parallel to the surface of the skin and perpendicular to the direction of travel to said shear waves.

13. A method for providing a quantitative indication of the properties of the outer layers of the skin, comprising the steps of:
inducing strains having an amplitude no greater than 30 micrometers in the skin to generate shear waves that propagate through the skin at a plurality of different frequencies;
measuring changes in the phase and amplitude for each frequency of the shear waves as they propagate through the skin;
determining the dynamic compliance of the skin for each frequency on the basis of the measured changes in phase and amplitude; and
displaying the determined dynamic compliance in the form of a graph.

14. The method of claim 5 wherein said dynamic compliance is comprised of an in-phase component $G_1$ and an out-of-phase component $G_2$, and said display is a graph of one component along one axis thereof and the other component along the other axis thereof.

15. The method of claim 14 further including the step of providing a display of a second graph wherein relative fluidity, defined as $G_2/G_1$, is represented on one axis of said second graph and total compliance, defined as $$\sqrt{G_1^2 + G_2^2},$$

is represented on the other axis.

16. The method of claim 5 wherein said strains have an amplitude in the range of 20–30 micrometers.

17. The method of claim 13 wherein said plurality of frequencies are within the range of about 8 Hz to about 1024 Hz.

18. The method of claim 13 wherein said strains are induced in a direction parallel to the surface of the skin and perpendicular to the direction of travel to said shear waves.

19. A method for providing a quantitative indication of properties of the stratum corneum layer of the skin, comprising the steps of:
inducing oscillatory deformations at the surface of the skin to generate shear waves that propagate along the stratum corneum layer of the skin, said deformations being induced at a plurality of different frequencies in the range of about 8 Hz to about 1024 Hz with a maximum amplitude of 30 micrometers and in a direction parallel to the surface of the skin and perpendicular to the direction propagation of said shear waves;
measuring changes in the phase and amplitude for different frequencies of the shear waves as they propagate through the stratum corneum layer; and
determining a modulus of elasticity and a modulus of viscosity for the stratum corneum layer of the skin on the basis of the measured changes.

20. The method of claim 19 wherein said changes are measured at a location that is remote from the location at which the oscillations are induced in the skin, in the direction that is parallel to the surface of the skin.

21. A method for measuring and quantitatively indicating viscoelastic properties of the uppermost layers of the skin, comprising the steps of:
inducing oscillations in the skin to generate shear waves that propagate through the skin;
measuring changes in the phase and amplitude of the shear waves as they propagate through the skin;
determining, from the measured changes in phase and amplitude, modulus of elasticity and viscosity constants descriptive of a mechanical skin model having three discrete elements respectively defined by said constants, wherein one of said constants is related to the rigidity of the stratum corneum layer of the skin, another of said constants is indicative of the viscosity of the stratum corneum, and a third constant is indicative of the viscosity of the viable epidermis layer which underlies the stratum corneum; and
displaying various complex moduli of elasticity and viscosity relationships.

22. The method of claim 21 wherein said oscillations are induced at a plurality of frequencies.

23. The method of claim 22 wherein said plurality of frequencies are within the range of about 8 Hz to about 1024 Hz.

24. The method of claim 21 wherein said oscillations occur in a direction parallel to the surface of the skin and perpendicular to the direction of travel of said shear waves.

25. A method for measuring and quantitatively indicating viscoelastic properties of the uppermost layers of the skin, comprising the steps of:
inducing oscillations in a direction parallel to the surface of the skin to generate shear waves that propagate through the skin in a direction perpendicular to the direction of said oscillations;
measuring changes in the phase and amplitude of the shear waves as they propagate through the skin;
determining modulus of elasticity and viscosity constants descriptive of a discrete-element mechanical skin model on the basis of the measured changes in phase and amplitude; and
displaying various complex moduli of elasticity and viscosity relationships.

26. The method of claim 25 wherein said oscillations are induced at a plurality of frequencies.

27. The method of claim 26 wherein said plurality of frequencies are within the range of about 8 Hz to about 1024 Hz.

28. The method of claim 25 wherein said changes are measured at a location that is remote from the location at which the oscillations are induced in the skin, in the direction that is parallel to the surface of the skin.

* * * * *

UNITED STATES PATENT AND TRADEMARK OFFICE
CERTIFICATE OF CORRECTION

PATENT NO. : 4,777,599

DATED : October 11, 1988

INVENTOR(S) : Peter L. Dorogi

It is certified that error appears in the above-identified patent and that said Letters Patent is hereby corrected as shown below:

On the first page of the patent under column 1, change the Assignee from "Gillette Company" to --The Gillette Company--; on the first page of the patent under "OTHER PUBLICATIONS", column 1, line 4, change "vol." to --Vol.--; on the first page of the patent under "OTHER PUBLICATIONS" under column 1, line 8, change "vol." to --Vol.--; on the first page of the patent under "OTHER PUBLICATIONS" under column 1, line 15, change "skin" to --Skin--; on the first page of the patent under "OTHER PUBLICATIONS" under column 2, line 12, change "vol." to --Vol.--; column 3, line 11, change "represenation" to --representation--; column 3, line 60, change "i.e." to --i.e.,--; column 4, line 30, change "i.e." to --i.e.,--; column 4, line 32, change "the"(first occurrence) to --and--; column 4, line 62, change "is" to --in--; column 5, line 3, change "e.g." to --e.g.,--; and column 6, lines 3-10, Table 1 should appear as follows:

TABLE I
EPIDERMAL MECHANICAL PARAMETERS;
QUANTITATIVE MEASURES OF
CONDITION EFFECTS ON THE EPIDERMIS

| TREATMENT | PARAMETERS |
|---|---|

Signed and Sealed this

Tenth Day of October, 1989

Attest:

DONALD J. QUIGG

Attesting Officer

Commissioner of Patents and Trademarks